United States Patent
Meudt et al.

(10) Patent No.: US 6,833,470 B2
(45) Date of Patent: Dec. 21, 2004

(54) METHOD FOR PRODUCING FORMYLPHENYLBORONIC ACIDS

(75) Inventors: Andreas Meudt, Floersheim-Weilbach (DE); Stefan Scherer, Buettelborn (DE); Frank Vollmueller, Frankfurt am Main (DE); Michael Erbes, Frankfurt (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/433,827

(22) PCT Filed: Nov. 30, 2001

(86) PCT No.: PCT/EP01/14014
§ 371 (c)(1),
(2), (4) Date: Jun. 5, 2003

(87) PCT Pub. No.: WO02/48155
PCT Pub. Date: Jun. 20, 2002

(65) Prior Publication Data
US 2004/0049050 A1 Mar. 11, 2004

(30) Foreign Application Priority Data

Dec. 14, 2000 (DE) .......................................... 100 62 305
Dec. 21, 2000 (DE) .......................................... 100 63 738

(51) Int. Cl.$^7$ ................................................. C07F 5/02
(52) U.S. Cl. ......................................................... 562/7
(58) Field of Search ............................................. 562/7

(56) References Cited

U.S. PATENT DOCUMENTS

| | | | |
|---|---|---|---|
| 5,157,149 A | 10/1992 | Samsel | 562/7 |
| 6,296,788 B1 | 10/2001 | Giffels et al. | 260/665 |
| 6,420,597 B2 * | 7/2002 | Vollmuller et al. | 562/7 |
| 6,576,789 B1 | 6/2003 | Haber et al. | 562/7 |
| 2002/0010332 A1 | 1/2002 | Vollmuller et al. | 544/229 |

FOREIGN PATENT DOCUMENTS

| | | |
|---|---|---|
| DE | 199 17 979 | 12/2000 |
| DE | 199 60 866 | 6/2001 |
| DE | 100 32 017 | 1/2002 |
| EP | 1 070 718 | 1/2001 |
| WO | 93/23391 | 11/1993 |

OTHER PUBLICATIONS

Tetrahedron Letters by Kobayashi et al vol. 39 pp. 7537–7540 1998.*

"Darstellung and strukturelle Charkterisierung der p–Formylbenzolboronsäure", H. Feulner, G. Linti, and H. Nöth, Chemischen Berichte, vol. 123 (1990), No. 9, pp. 1841–1843.

"Efficient, simple Procedures for the Large–Scale Preparation of Building Blocks for Angiotensin (II) Receptor Antagonists", H. Jendralla, A. Wagner, and J. Wunner, Liebigs Annalen, 1995, pp 1253–1257.

* cited by examiner

*Primary Examiner*—Samuel Barts
(74) *Attorney, Agent, or Firm*—Richard P. Silverman

(57) ABSTRACT

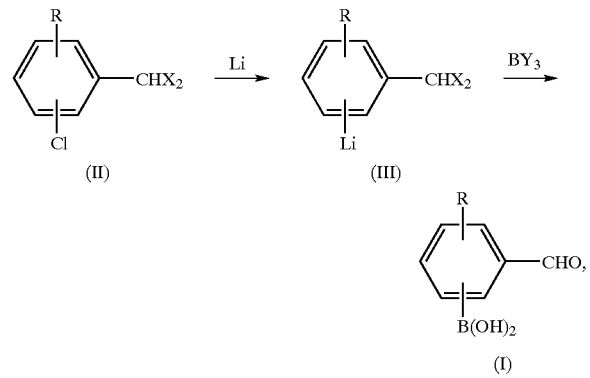

A process for preparing formylphenylboronic acids of the formula (I) by reaction of protected chlorobenzaldehydes of the formula (II) with lithium in an inert solvent to form compounds of the formula (III) and subsequent reaction with a boron compound of the formula $BY_3$ to give compounds of the formula (I).

20 Claims, No Drawings

METHOD FOR PRODUCING FORMYLPHENYLBORONIC ACIDS

The invention relates to a process for preparing formylphenylboronic acids of the formula (I).

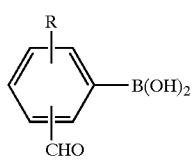

Ortho-, meta- and para-formylphenylboronic acids are versatile building blocks in organic synthesis and are important intermediates in the synthesis of active compounds in the agrochemical and pharmaceutical industries, but the compounds are of especially high efficiency and importance as enzyme stabilizers, inhibitors and bactericides.

Despite the great commercial interest in these compounds because of the abovementioned applications, only a few, expensive routes for preparing them have been described in the literature.

Boronic acids are prepared quite generally by reacting organometallic compounds (e.g. Grignard compounds or organolithium compounds) with boron trihalides or trialkyl borates. Owing to the reactivity of the formyl group toward organometallic compounds, this procedure is only possible for preparing formylphenylboronic acids when the formyl group is protected appropriately beforehand. As raw materials, it is therefore necessary to use p-halobenzaldehydes which are, for example, acetalized and subsequently reacted to form the organometallic reagent.

Nöth et al. (Chem. Ber. 1990, 1841–1843) convert p-bromobenzaldehyde into the diethyl acetal, convert this into the corresponding Grignard reagent by means of magnesium turnings in tetrahydrofuran (THF) and, after reaction with tri-n-butyl borate, obtain formylphenylboronic acid in a yield of 70%. A disadvantage of this synthesis is the high price of bromobenzaldehyde compared to chlorobenzaldehyde, the need for ultrasonic activation in the preparation of the Grignard reagent and the use of the expensive tributyl borate; in addition, complicated purification procedures have to be employed (e.g. via the hydrolysis product 1-butanol).

Jendralla et al. (Liebigs Ann. 1995, 1253–1257) achieve an improvement to 78% by means of process improvements in the same synthetic sequence, but here, too, the abovementioned disadvantages remain.

Significantly better yields (up to 99%) were achieved by Kobayashi et al. by reaction of bromobenzaldehyde diethyl acetal with n-butyllithium and subsequent reaction with triisopropyl borate, but the high prices of bromobenzaldehyde, triisopropyl borate and butyllithium stand in the way of an economically interesting process.

There is therefore a need to develop a process for preparing formylphenylboronic acids which starts out from advantageous starting materials which are readily available commercially and makes it possible to obtain the target products in good yields and high purities by reaction with cheap boron compounds.

It was firstly established that the necessary Grignard compounds cannot be obtained from various chlorobenzaldehyde acetals by reaction with magnesium in various ethers by methods of the prior art. In the German patent application DE-A-199 60 866, which is not a prior publication, it was found that the Grignard compounds can be obtained in good yields by addition of transition metal catalysts and simultaneous mechanical activation of the magnesium. Reaction with trimethyl borate results in corresponding formylphenylboronic acids in good yields. This is an economically very interesting method of preparation which, however, requires high capital costs and places considerable demands on plant construction due to the mechanical activation of the magnesium which is required. At the same time, the products contain traces of the transition metals used in the ppm range which, depending on the application (pharmaceuticals, enzyme inhibitors), have to be removed quantitatively by costly methods.

It is therefore an object of the present invention to provide a simple and economical process for preparing formylphenylboronic acids which starts out from advantageous starting materials which are readily available commercially and makes do without the use of transition metal catalysts and without high capital costs for plant construction. At the same time, the process should give the products in very high yields and purities.

The present invention achieves these objects and provides a process for preparing formylphenylboronic acids of the formula (I) by reaction of protected chlorobenzaldehydes of the formula (II) with lithium metal in an inert solvent to form compounds of the formula (III) and subsequent reaction with a boron compound of the formula $BY_3$ to give compounds of the formula (I)

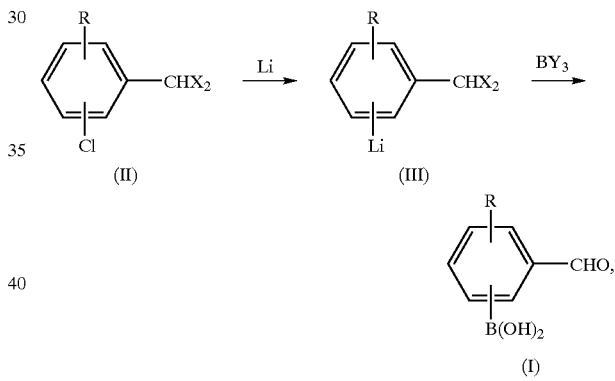

where Y is a straight-chain or branched $C_1$–$C_6$-alkoxy or $C_1$–$C_5$-dialkylamino group, halogen or a $C_1$–$C_6$-alkylthio group, and R is H or a $C_1$–$C_5$-alkyl or $C_1$–$C_5$-alkoxy radical.

The radical $CHX_2$ is preferably an acetal of the formula (IV) or (V)

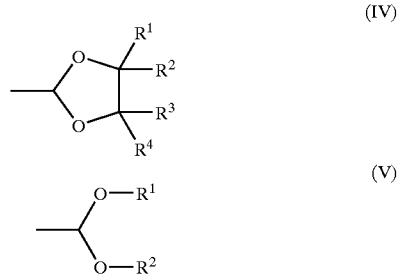

where $R^1$ to $R^4$ are identical or different and are each hydrogen, $C_1$–$C_{12}$-alkyl or phenyl, or $R^1$ and $R^2$ together or $R^1$ and $R^3$ together form a 5- or 6-membered aliphatic or aromatic ring; or an oxazolidine of the formula (VI)

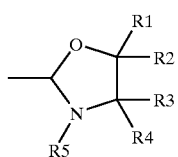

(VI)

or an aminal of the formula (VII)

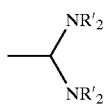

(VII)

where $R^1$ and $R^4$ are as defined above and $R^5$ and $R'$ are each $C_1$–$C_6$-alkyl or aryl.

As starting compounds of the formula (II), it is possible to use protected ortho-, meta- or para-chlorobenzaldehydes.

Although the lithium metal used according to the invention is an expensive raw material on the basis of its mass, the price difference compared to magnesium on the basis of molar amounts used is comparatively small. In the present process, the metal is placed as a dispersion, powder, turnings, sand, granules, pieces, bars or in another form together with a suitable solvent in a reaction vessel and is reacted with the protected chlorobenzaldehyde. Suitable inert solvents are all solvents which react neither with the lithium metal nor with the lithiated aromatic formed under the conditions of the process of the invention, in particular aliphatic or aromatic ethers, tertiary amines or hydrocarbons, e.g. THF, diethyl ether, diisopropyl ether, di-n-butyl ether, toluene, cyclohexane or dioxane or mixtures of the inert solvents in question.

The reaction of lithium metal with protected chlorobenzaldehydes is carried out at temperatures in the range from −100° C. to +35° C., since the reaction proceeds too slowly at lower temperatures but at higher temperatures the lithium aryls formed attack and cleave the, for example, acetal, aminal or oxazolidine function. Preferred reaction temperatures are therefore in the range from −70 to +10° C., particularly preferably from −55 to +5° C.

The reaction of lithium with compounds of the formula (II) is generally complete after from 3 to 18 hours, in particular from 4 to 10 hours, although in some cases, depending on the nature of the protected chlorobenzaldehyde used and the solvent employed, the reaction can proceed significantly more slowly, resulting in poor space-time yields. The rate of this reaction can be increased considerably by the presence of organic redox catalysts such as biphenyl, naphthalene or other organic compounds which rapidly take up electrons from the Li metal and transfer them quickly and efficiently to the C—Cl bond of the protected chlorobenzaldehyde. The redox catalysts are added in amounts of from 0 to 5 mol %.

The molar ratio of lithium to the compound of the formula (II) is usually in the range from 1.9:1 to 8:1, but larger excesses can also be used when this is, for example, advantageous for reasons of the apparatus employed, e.g. in pumped circulation apparatuses.

The concentration of the lithium compound in the solvent can be from 0.5 to 50% by weight, preferably from 5 to 35% by weight, particularly preferably from 15 to 30% by weight. The protected chlorobenzaldehyde can either be metered in or (especially in the case of relatively large Li pieces) can all be placed in the reaction vessel initially.

The reaction of the resulting organolithium compounds of the formula (III) with the boron compounds is, to achieve high selectivity, carried out at low temperatures in the range from +20 to −110° C., preferably from 0 to −80° C. It is possible either to add the boron compounds as liquids or solutions to the solution of the organolithium compound or to add the solution of the organolithium compound to the initially charged boron compound (which may, if desired, have been initially charged as a solution in hydrocarbons or ethers). It is advantageous to use a small excess, in particular an excess in the range from 5 to 50%, of boron compound.

Suitable boron compounds are, for example, boron halides such as $BBr_3$, $BF_3$, $BCl_3$ or boric esters, e.g. trimethyl borate, triisopropyl borate or tributyl borate; it is likewise possible to use mixed haloboric esters. Amines or thio compounds of boron, for example tris(diethylamino)borane or tris(n-butylthio)borane, can likewise be used.

After the reaction mixtures have thawed to room temperature, various work-up methods are suitable, for example hydrolysis by addition of water, adjustment of the pH to a slightly acidic region (2.5–6.5), distilling off the solvents, filtration and drying of the product. For economic reasons, it is of great interest to obtain the solvent used in the lithiation in water-free form and thus reuse it directly in the lithiation; thus, it can be obtained by distillation from the reaction mixture with simultaneous addition of a relatively high-boiling solvent. For example, diethyl ether can be replaced by cyclohexane or THF can be replaced by toluene.

Before the formylphenylboronic acids are separated off from the reaction mixture, for example by filtration or centrifugation, water-soluble solvents such as THF should preferably be separated off by, for example, distillation, since otherwise the solubility of the products in water is increased and the yields are correspondingly reduced. The pH of the hydrolysis mixture is firstly in the alkaline region and is brought to a value in the range from 7.5 to 1.0 before the product is isolated or before water-soluble solvents are distilled off, in order to prevent secondary reactions such as Cannizzaro reactions. Preference is here given to pH ranges from 6.0 to 3.0, particularly preferably the pH of the free boronic acid. Filtration or centrifugation of the products is advantageously carried out at temperatures in the range from −10 to +75° C. Owing to their oxidation sensitivity, the formylphenylboronic acids obtained have to be dried under protective gas and under reduced pressure and at mild temperatures, preferably in the range from 20 to 80° C.

When all work is carried out under protective gas, the product is obtained in very pure form (>99%, HPLC a/a) and can in most cases be used further without further purification.

For specific applications, purification is necessary and can be carried out, for example, by dissolution in aqueous sodium hydroxide at 0–30° C., extraction with toluene or another hydrocarbon or ether and subsequent precipitation by acidification. Such appropriate purification methods are described, for example, in the German patent application DE-A-10 032 017.1 which is not a prior publication.

The process of the invention is illustrated by the following examples, without the invention being restricted thereto:

EXAMPLE 1

3.52 g of lithium turnings and 180 g of THF are placed in a reaction vessel at −50° C. 53.6 g of 4-chlorobenzaldehyde diethyl acetal are added dropwise over a period of 90 minutes. After stirring for another 2 hours, the mixture is cooled to −70° C. and 31.2 g of trimethyl borate dissolved in 60 ml of THF are added dropwise at this temperature over a period of 15 minutes. The mixture is allowed to thaw overnight. At 0° C., 250 g of water are added and the pH is adjusted to 4.5 using 26.5 g of 36% HCl. The water-containing THF is distilled off as completely as possible under a slight vacuum. The resulting suspension is cooled to 10° C. and filtered with suction at 10° C. The product is washed with a little ice water and dried at 40° C. in a gentle stream of nitrogen. The yield of pure 4-formylphenylboronic acid is 35.8 g (95.6%).

EXAMPLE 2

4.3 g of lithium turnings, 0.03 g of biphenyl and 450 g of THF are placed in a reaction vessel at −50° C. 53.6 g of 4-chlorobenzaldehyde ethylene glycol acetal are added dropwise over a period of 90 minutes. After stirring for another 7 hours, the mixture is cooled to −60° C. and 32.2 g of trimethyl borate dissolved in 30 ml of THF are added dropwise at this temperature over a period of 30 minutes. The mixture is allowed to thaw overnight. At 0° C., 250 g of water are added and the pH is adjusted to 4.5 using 26.5 g of 36% HCl. The water-containing THF is distilled off as completely as possible under a slight vacuum. The resulting suspension is cooled to 10° C. and filtered with suction at 10° C. The product is washed with a little ice water and dried at 40° C. in a gentle stream of nitrogen. The yield of pure 4-formylphenylboronic acid is 33.8 g (90.1%); the somewhat lower yield compared to the first experiment can be explained by the dissociation product glycol, which increases the solubility of the product in the aqueous phase.

EXAMPLE 3

The preparation of the lithium compound was carried out by a method analogous to example 1, but in this case a 1:1 mixture of THF and toluene was used as solvent. The resulting Li compound was reacted at −70° C. with 1.2 equivalents of a commercially available solution of $BCl_3$ in toluene. The yield of 4-formylphenylboronic acid was 79% in this case.

EXAMPLE 4

Example 2 was repeated with addition of 0.2 mol % of biphenyl, as a result of which the further stirring time was able to be halved to 2 hours. The yield was 89% in this case.

EXAMPLE 5

The preparation of the Li compound was carried out by a method analogous to example 2 in the solvent toluene with addition of 0.25% of biphenyl; the further stirring time had to be increased to 14 hours. Yield: 83%.

EXAMPLE 6

The procedure of example 1 was repeated using 3-chlorobenzaldehyde diethyl acetal as starting material to give 3-formylphenylboronic acid in a yield of 91.5%.

EXAMPLE 7

The procedure of example 1 was repeated using 2-chlorobenzaldehyde diethyl acetal as starting material to give 2-formylphenylboronic acid in a yield of 83%.

EXAMPLE 8

3.52 g of lithium turnings and 180 g of THF are placed in a reaction vessel at −50° C. 53.7 g of 3-chlorobenzaldehyde N,N'-dimethylethylenediaminal (255 mmol) are added drop- wise over a period of 90 minutes. After stirring for a further 2 hours, the mixture is cooled to −50° C. and 31.2 g of trimethyl borate dissolved in 60 ml of THF are added dropwise at this temperature over a period of 15 minutes. The mixture is allowed to thaw overnight. At 0° C., 290 g of water are added and the pH is adjusted to 3.9 using 36.9 g of 37% HCl. The water-containing THF is distilled off as completely as possible under a slight vacuum (at atmospheric pressure to ensure complete dissociation of the aminal). The resulting suspension is cooled to 10° C. and filtered with suction at 10° C. The product is carefully washed with ice water and dried at 40° C. in a gentle stream of nitrogen. The yield of pure 3-formylphenylboronic acid is 34.5 g (92.1%).

What is claimed is:

1. A process for preparing formylphenylboronic acids of formula (I),

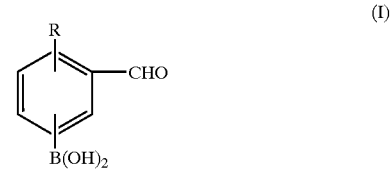

said process comprising:

reacting in an inert solvent at a temperature in the range from −100° C. to +35° C. protected chlorobenzaldehydes of formula (II)

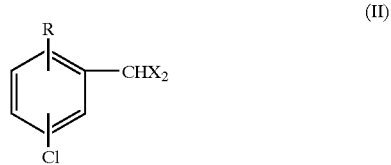

with lithium metal to form organolithium compounds of formula (III)

and subsequently reacting the organolithium compounds of formula (III) with a boron compound of the formula $BY_3$ to give compounds of the formula (I)

where Y is a straight-chain or branched $C_1$–$C_6$-alkoxy or $C_1$–$C_5$-dialkylamino group, halogen or a $C_1$–$C_6$-alkylthio group, and R is H or a $C_1$–$C_6$-alkyl or $C_1$–$C_6$-alkoxy, and the $CHX_2$ is an acetal of the formula (IV) or (V)

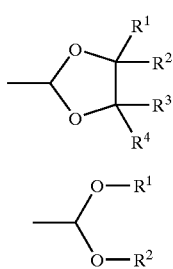

(IV)

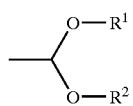

(V)

where $R^1$ to $R^4$ are identical or different and are each hydrogen, $C_1$–$C_{12}$-alkyl or phenyl, or $R^1$ and $R^2$ together or $R^1$ and $R^3$ together form a 5- or 6-membered aliphatic or aromatic ring; or an oxazolidine of the formula (VI)

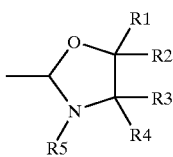

(VI)

or an aminal of the formula (VII)

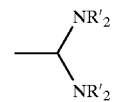

(VII)

where $R^1$ and $R^4$ are as defined above and $R^5$ and $R'$ are each $C_1$–$C_6$-alkyl or aryl, and hydrolyzing the compounds of formula (I) to form said formylphenylboronic acids.

2. The process as claimed in claim 1, wherein the ratio of lithium metal: compound of the formula (II) ranges from 1.9:1 to 8:1.

3. The process as claimed in claim 1, wherein the lithium metal is selected from the group consisting of a dispersion, powder, sand, turnings, pieces, granules, and mixtures thereof.

4. The process as claimed in claim 1, wherein the inert solvent is selected from the group consisting of aliphatic or aromatic ethers, tertiary amines, hydrocarbons and mixtures thereof.

5. The process as claimed in claim 1, wherein the reaction of protected chlorobenzaldehydes of formula (II) with lithium metal is carried out in the presence of organic redox catalysts.

6. The process as claimed in claim 1, wherein the subsequently reacting step is carried out at temperatures ranging from +20° C. to –110° C.

7. The process as claimed in claim 1, wherein the boron compound is used in an excess relative to the organolithium compounds.

8. The process as claimed in claim 1, wherein said inert solvent comprises a water soluble solvent and said process further comprises distilling the water soluble solvent and separating off the formylphenylboronic acids.

9. The process as claimed in claim 8, wherein pH is adjusted to a value ranging from 7.5 to 1.0 before distilling the water soluble solvent.

10. The process as claimed in claim 8, wherein said separating off of the formylphenylboronic acids is selected from the group consisting of filtration, centrifugation, and mixtures thereof at temperatures ranging from –10 to +75° C.

11. The process as claimed in claim 1, further comprising drying the formylphenylboronic acids under protective gas.

12. The process as claimed in claim 9, wherein the formylphenylboronic acids are separated off from the reaction mixture by filtration or centrifugation at temperatures in the range from –10 to +75° C.

13. The process as claimed in claim 1, wherein the subsequent reaction of lithium with the protected chlorobenzaldehydes is carried out at a temperature ranging from –100° C. to +35° C.

14. The process as claimed in claim 13, wherein the inert solvent is selected from the group consisting of aliphatic or aromatic ethers, tertiary amines, hydrocarbons, and mixtures thereof.

15. The process as claimed in claim 14, wherein the reaction of protected chlorobenzaldehydes of the formula (II) with lithium metal is carried out in the presence of organic redox catalysts.

16. The process as claimed in claim 15, wherein the subsequent reaction of the organolithium compounds of the formula (III) with the boron compounds $BY^3$ is carried out at temperatures ranging from +20° C. to –110° C.

17. The process as claimed in claim 16, wherein the boron compound is used in an excess relative to the organolithium compounds.

18. The process of claim 14, wherein said inert solvent is a water-soluble solvent and said process further comprises distilling said water-soluble solvent and separating off the formylphenylboronic acids, wherein said water-soluble solvent is distilled before the formylphenylboronic acids of the formula (I) are separated off.

19. The process as claimed claim 18, further comprising drying the formylphenylboronic acids of the formula (I) under protective gas, optionally, under reduced pressure.

20. The process of claim 11, wherein said drying is carried out under reduced pressure.

* * * * *